United States Patent
Tirtowidjojo

(10) Patent No.: US 9,598,334 B2
(45) Date of Patent: Mar. 21, 2017

(54) PROCESS FOR THE PRODUCTION OF CHLORINATED PROPENES

(71) Applicant: Blue Cube IP LLC, Midland, MI (US)

(72) Inventor: Max M. Tirtowidjojo, Lake Jackson, TX (US)

(73) Assignee: BLUE CUBE IP LLC, Midland, MI (US)

( * ) Notice: Subject to any disclaimer, the term of this patent is extended or adjusted under 35 U.S.C. 154(b) by 14 days.

(21) Appl. No.: 14/429,263

(22) PCT Filed: Sep. 13, 2013

(86) PCT No.: PCT/US2013/059680
§ 371 (c)(1),
(2) Date: Mar. 18, 2015

(87) PCT Pub. No.: WO2014/046977
PCT Pub. Date: Mar. 27, 2014

(65) Prior Publication Data
US 2015/0266798 A1    Sep. 24, 2015

Related U.S. Application Data

(60) Provisional application No. 61/703,374, filed on Sep. 20, 2012.

(51) Int. Cl.
*C07C 17/10* (2006.01)
*C07C 17/25* (2006.01)
*C07C 17/04* (2006.01)

(52) U.S. Cl.
CPC ............. *C07C 17/25* (2013.01); *C07C 17/04* (2013.01); *C07C 17/10* (2013.01)

(58) Field of Classification Search
CPC .................................................. C07C 17/10
USPC .................... 570/220, 234, 241, 246, 252
See application file for complete search history.

(56) References Cited

U.S. PATENT DOCUMENTS

| | | |
|---|---|---|
| 2,119,484 A | 5/1938 | Levine et al. |
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl et al. |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |

(Continued)

FOREIGN PATENT DOCUMENTS

| | | |
|---|---|---|
| CH | 609022 | 6/1974 |
| CN | 101215220 | 7/2008 |
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |

(Continued)

OTHER PUBLICATIONS

Michigan Technological Univ., "Free-Radical Chlorination with Sulfuryl Chloride", Nov. 15, 2001, 1-7.
Bai, et al., "Isomerization of Tetrachloropropene to Promote Utilization Ratio of Triallate Raw Materials", Petrochemical Technology & Application, 2007, 25(1).

(Continued)

*Primary Examiner* — Elvis O Price
(74) *Attorney, Agent, or Firm* — Polsinelli PC

(57) ABSTRACT

Processes for the production of chlorinated propenes are provided. The present processes make use of 1,2-dichloropropane, a by-product in the production of chlorohydrin, as a low cost starting material, alone or in combination with 1,2,3-trichloropropane. At least one dehydrochlorination is conducted in the gas phase, and is the first process step. The present processes can also generate anhydrous HCl as a byproduct that can be removed from the process and used as a feedstock for other processes, providing further time and cost savings.

13 Claims, 1 Drawing Sheet

(56) References Cited

U.S. PATENT DOCUMENTS

| | | |
|---|---|---|
| 4,661,648 A | 4/1987 | Franklin |
| 4,702,809 A | 10/1987 | Mueller |
| 4,714,792 A | 12/1987 | Mueller et al. |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo et al. |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi et al. |
| 2002/0087039 A1 | 7/2002 | Tung et al. |
| 2002/0110711 A1 | 8/2002 | Boneberg et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0197842 A1 | 8/2007 | Tung |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0030249 A1 | 1/2009 | Merkel et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54079207 | 6/1979 |

(56) References Cited

FOREIGN PATENT DOCUMENTS

| | | |
|---|---|---|
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Boualy, et al., "Kharasch Addition of Tetrachloromethane to Alkenes Catalyzed by Metal Acetylacetonates", "Kharasch Addition of Tetrachloromethane to Alkenes Catalyzed by Metal Acetylacetonates".

Chai, et al., "Study of Preparation of 1,1,1,3-tetrachloropropane", Zhejiang Chemical Industry, 2010, pp. 1-3, 41(5).

Cristiano, et al., "Tetraalkylphosphonium Trihalides. Room Temperature Ionic Liquids as Halogenation Reagents", J. Org. Chem., 2009, pp. 9027-9033, 74.

Evstigneev, et al., "Initiated Chlorination of Tetrachloropropane", Khim. Prom., 1984, pp. 393-394, 16(7).

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39(5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.l. The Peroxide-Catalyzed Chlorination of Hydrocarbons", JACS, 1939, pp. 2142-2150, 61.

Khusnutdinov, et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3-C4", 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry,Feb. 1, 1941, pp. 176-181, 33(2).

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)Cl Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, WI-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

(56) References Cited

OTHER PUBLICATIONS

Tanuma, et al., "Partially Fluorinated Metal Oxide Catalysts for a Friedel-Crafts-type Reaction of Dichlorofluoromethane with Tetrafluoroethylene", Catal. Lett., 2010, pp. 77-82, 136.

Tobey, et al., "Pentachlorocyclopropane", Journal of the American Chemical Society, Jun. 1, 1996, pp. 2478-2481, 88(11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

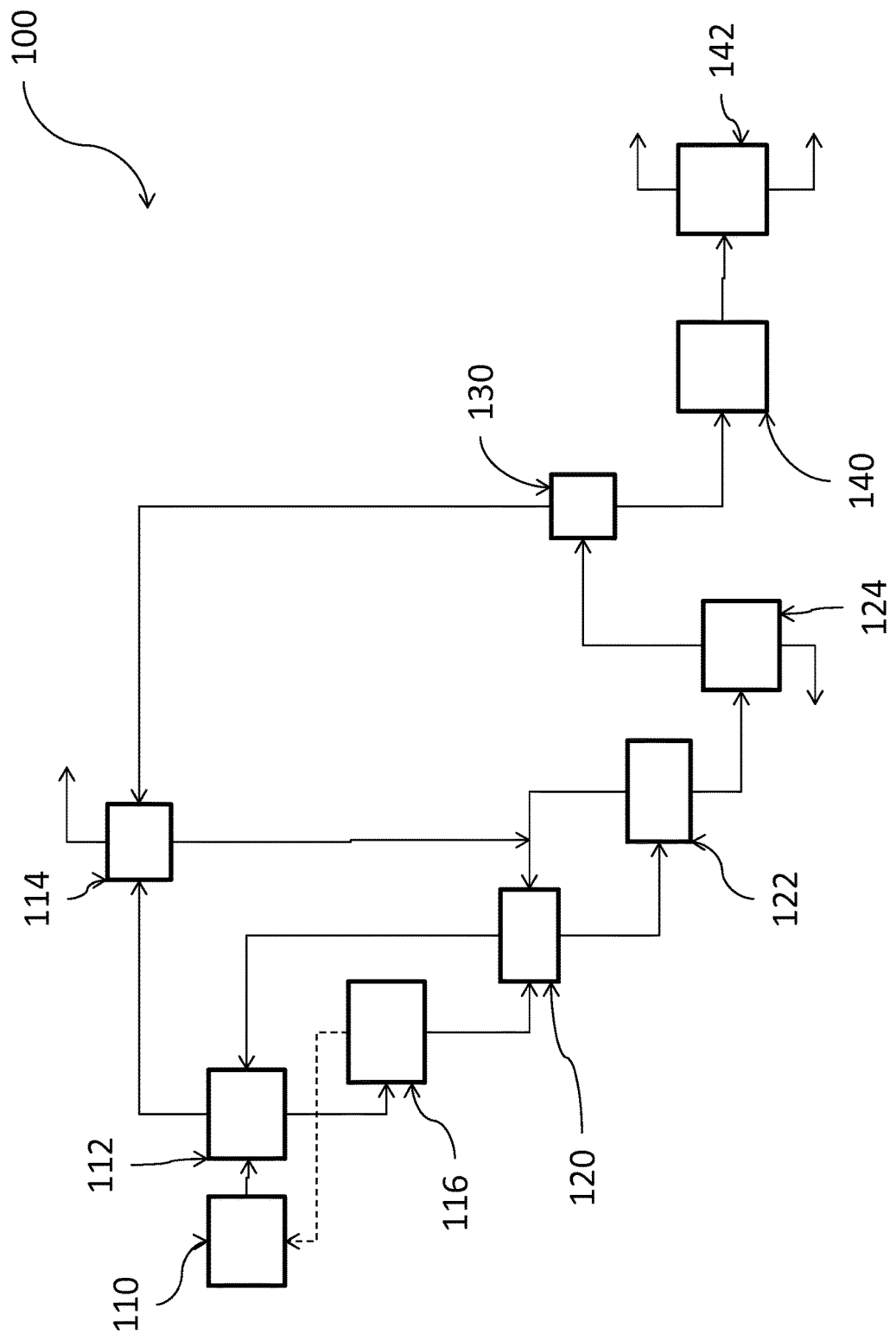

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3, 3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. This may be due at least in part to the fact that conventional processes for their manufacture may require the use of starting materials that are prohibitively expensive to be economically produced by manufacturers on the large scale required to be useful as feedstocks. Additionally, conventional processes may require multiple chlorination and dehydrochlorination steps to arrive at a desired level of chlorination in the final product. Dehydrochlorination steps are typically conducted with an aqueous base, and result in the production of large quantities of waste water containing large quantities of sodium chloride and/or chlorinated organics. Treatment of this waste water is time consuming and expensive, and results in the recovery of low value by-products.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly in starting materials, processing time, utility costs and/or capital costs required to implement and maintain the process. Generation of byproducts having a higher value than sodium chloride, or really any value, would be a further advantage if provided in such a process.

BRIEF DESCRIPTION

The present invention provides efficient processes for the production of chlorinated propenes. Advantageously, the processes make use of 1,2-dichloropropane, a by-product in the production of chlorohydrin, as a low cost starting material, alone or in combination with 1,2,3-trichloropropane. At least one dehydrochlorination step is conducted in the gas phase, and is the first process step. Because a dehydrochlorination occurs first, a next chlorination occurs across a double bond, and so, may not require the use of catalysts so that cost savings are provided. In some embodiments, the gas phase dehydrochlorination may be conducted at an elevated temperature, e.g., greater than 150° C., and without the use of catalyst. Because the use of catalyst can be avoided in the gas phase dehydrochlorination of PDC, operating costs may be saved, i.e., that may otherwise be incurred for catalyst replacement and/or reactor downtime due to fouling. In these, and other, embodiments, the gas phase dehydrochlorination may occur at temperatures lower than those conventionally utilized for gas phase dehydrochlorinations, e.g., less than 600° C. Anhydrous HCl is produced as a byproduct by the at least one gas phase dehydrochlorination, and in some embodiments, additional dehydrochlorinations may also be conducted catalytically in rather than using caustic. By processing lesser amounts of chlorinated propane intermediates through caustic cracking than conventional processes even greater amounts of anhydrous HCl can be recovered from the process rather than the lower value NaCl produced by multiple caustic cracking steps. Less waste water is thus generated, providing further time and cost savings.

In one aspect, the present invention provides a process for the production of chlorinated propenes from one or more chlorinated alkanes. The process comprises at least one gas phase dehydrochlorination as a first step. The gas phase dehydrochlorination may be carried out at an elevated temperature, e.g., greater than 150° C., without the use of catalyst. In some embodiments, the gas phase dehydrochlorination of PDC is carried out at temperatures lower than those called for by conventional gas phase dehydrochlorinations, e.g., less than 600° C. The one or more chlorinated alkanes comprise 1,2-dichloropropane, and may further comprise 1,2,3-trichloropropane. Additional dehydrochlorinations used in the process may be carried out in the liquid or gas phase, and may be conducted using catalysts or caustic. Anhydrous HCl is produced as a byproduct by the at least one gas phase dehydrochlorination, and greater amounts can be recovered by conducting one or more additional dehydrochlorinations catalytically, in the gas phase. Further, one or more reactants may be generated within or upstream of the process.

DESCRIPTION OF THE FIGURES

FIG. 1 shows a schematic representation of a process according to one embodiment.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane, "TCP" may be used as an abbreviation for 1,2,3-trichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes. The present processes comprise conducting at least one dehydrochlorination step in the gas phase on one or more chlorinated propanes comprising PDC. The use of PDC, a byproduct in many chlorohydrin and allyl chloride processes, as a starting material is economically more attractive than disposing of it via incineration, as may be done in connection with some conventional chlorohydrin and allyl chloride processes.

The gas phase dehydrochlorination of PDC occurs as a first step of the process, and in some embodiments, may take place at an elevated temperature to enhance the reaction rate, so that catalysts need not be utilized. Cost savings are thus provided, since catalyst need not be purchased, or replaced, that can occur when catalysts are utilized. Any other dehydrochlorinations used in the course of the process may be conducted in either the gas or liquid phase.

In some embodiments, the conversion, or cracking rate of PDC will desirably be less than 70%, or less than 60%, or less than 50%, or even less than 40%. Desirably, the cracking rate or conversion of PDC will be greater than greater than 30%, or greater than 40%, or greater than 50%, or greater than 60%, or up to about 70%. In other embodiments, the conversion of PDC will be from 30% to 70%, or from 40% to 60%. At conversions higher than 70%, it is expected that large quantities of byproducts may be produced, requiring more frequent cleaning of the reactor, and thus down time. At conversions lower than 30%, it is expected that the production rate will not be optimized, yield will be lower, and the production equipment will not be operating at its full potential.

The gas phase dehydrochlorination(s) may be conducted at elevated temperatures, e.g., of 150° C., with accommodations made via the length of the reactor or processing time to provide an adequate reaction time. In some embodiments, the gas phase dehydrochlorination may desirably be conducted at elevated temperatures, e.g. of 150° C., or 175 C, or 200 C.°, or 225° C., or 250° C., or 275° C. or even 300° C. or greater. The temperature should be elevated enough to see an improvement in process yield and/or selectivity, rather than a decline in the same, as may result from e.g., reactant or product decomposition. At temperatures greater than, e.g., 600° C., for example, significant decomposition of dichloropropane or its products, and/or the formation of undesirable amounts of by products, may be expected to occur, and so, in some embodiments, if the reaction occurs at an elevated temperature, the temperature will desirably not exceed 600° C., or 575° C., or 550° C.

In some embodiments, the gas phase dehydrochlorination may desirably occur at temperatures between 150° C. and 600° C. or between 175° C. and 600° C. or between 200° C. and 600° C., or between 225° C. and 600° C. or between 250° C. and 600° C. or between 275° C. and 600° C. In other embodiments, the gas phase dehydrochlorination may occur at temperatures between 150° C. and 575° C. or between 175° C. and 575° C. or between 200° C. and 575° C., or between 225° C. and 575° C. or between 250° C. and 575° C. or between 275° C. and 575° C. In yet other embodiments, the gas phase dehydrochlorination may desirably occur at temperatures between 150° C. and 550° C. or between 175° C. and 550° C. or between 200° C. and 550° C., or between 225° C. and 550° C. or between 250° C. and 550° C. or between 275° C. and 550° C.

Any other dehydrochlorinations utilized in the process may occur in either the gas or liquid phase, and may occur in the presence of caustic, or catalyst in the case of additional gas phase dehydrochlorination. In some embodiments of the present processes, one or more additional gaseous catalytic dehydrochlorinations are utilized, in addition to the initial gaseous dehydrochlorination of PDC, and as a result, such processes may provide a further reduction of caustic cracking steps as compared to conventional processes. In such embodiments, additional amounts anhydrous HCl may be recovered. Anhydrous HCl is of greater value than the sodium chloride that would be produced as byproducts) if conventional caustic cracking steps were utilized. The present process thus results in the production of a by-product that may either be sold or used as a feedstock for other processes, e.g., ethylene oxyhalogenation to produce ethylene dichloride. If the use of catalysts is desired, suitable dehydrochlorination catalysts include, but are not limited to, aluminum chloride ($AlCl_3$), ferric chloride ($FeCl_3$), or combinations of these, may be used as a substitute to caustic.

In other embodiments, additional dehydrochlorination steps of the present process may be conducted in the presence of a liquid caustic. Many chemical bases are known in the art to be useful for this purpose, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts can also be added to improve the dehydrochlorination reaction rate with these chemical bases.

Any chlorinations utilized in the process may be conducted in the liquid phase with or without the use of catalysts, however, catalysts can be used if desired, to enhance the present process. For example, free radical initiators are suitable for use, and those of ordinary skill in the art are aware of many. Known free radical catalysts or initiators are desirably used to enhance the present process. Such catalysts may typically comprise one or more chlorine, peroxide or azo-(R—N=N-R') groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated and/or fluorinated propene(s), within the design limitations of the reactor.

Furthermore, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same, does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4), 333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable catalysts/initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of not being able to propagate competitive processes (e.g., the free radical chlorination of PDC to TCP (and its isomers) and tetrachloropropanes). In addition, compounds, such as azobisisobutyronitrile (AIBN) or 1,1'-azobis(cyclohexanecarbonitrile (ABCN), may have utility in effecting the chlorination of PDC to trichloropropanes and tetrachloropropanes under the conditions of this invention. Combinations of any of these may also be utilized.

The process or reactor zone may be subjected to pulse laser or continuous UV/visible light sources at a wavelength suitable for inducing photolysis of the free radical catalyst/initiator, as taught by Breslow, R. in *Organic Reaction Mechanisms* W. A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

Ionic chlorination catalysts may also be used to catalyze the chlorinations performed in the present process. Ionic chlorination catalysts remove a chlorine and hydrogen from adjacent carbon atoms, the adjacent carbon atoms form a double bond, and HCl is released. A chlorine is then added back, replacing the double bond, to provide a more highly chlorinated alkane. Ionic chlorination catalysts are well known to those or ordinary art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any free radical chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected that useful concentrations of the free radical initiator or ionic chlorination catalyst will range from 0.001% to 20% by weight, or from 0.01% to 10%, or from 0.1% to 5 wt. %. If a dehydrochlorination catalyst is utilized for one or more dehydrochlorination steps, useful concentrations may range from 0.01 wt. % to 5 wt. %, or from 0.05 wt. % to 2 wt. % at temperatures of 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Relative concentrations of each catalyst/base are given relative to the feed, e.g. 1,2-dichloropropane alone or in combination with 1,2,3-trichloropropane.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

The present process can make use of one or more chlorinated alkanes to produce the desired chlorinated propenes. Desirably, the one or more chlorinated alkanes comprise 1,2-dichloropropane, which may be available at low cost due to its production as a by-product in many chlorohydrin and allyl chloride processes. The process feedstock may also comprise trichloropropane, or other chlorinated alkanes, if desired. And, the one or more chlorinated alkanes may be generated within or upstream of the process, if desired, e.g., as a byproduct in a chlorohydrin process, or by any other methods known to those of ordinary skill in the art.

Any chlorinated propene may be produced using the present method, although those with 3-5 chlorine atoms are more commercially sought after, and production of the same may thus be preferred in some embodiments. In some embodiments, the process may be used in the production of 1,1,2,3-tetrachloropropene, which is highly sought after as a feedstock for refrigerants, polymers, biocides, etc.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, mechanical mixing, etc.

That being said, the particular conditions employed at each step described herein are not critical, and are readily determined by those of ordinary skill in the art. What is important is that PDC is utilized as a starting material, the dehydrochlorination thereof occurs in the gas phase, as a first processing step. It can be advantageous, in some embodiments, for this initial gaseous dehydrochlorination to occur at temperatures of from 150° C. to 600° C. The order of the following reaction steps is unimportant, and those of ordinary skill in the art will readily be able to determine suitable equipment for each step, as well as the particular conditions at which the chlorination, dehydrochlorination, separation, drying, and isomerization steps may be conducted.

In one exemplary embodiment, a feed stream comprising PDC is first fed to a vapor phase dehydrochlorination reactor, e.g., such as a continuous long reaction tubing arranged in a coil and heated in a fired box. A shell and multitube reactor wherein the tubes are filled with a fixed bed catalyst suitable for catalytically cracking the PDC in the vapor phase can also be used. For reasons of process efficiency, the use of a reactor capable of accommodating a continuous process is preferred.

Suitable reaction conditions for this initial vapor-phase dehydrochlorination reactor include, e.g., temperatures of from ambient temperature (e.g., 200° C.) to 700° C., or from 250° C. to 600° C., or from 300° C. to 500° C. Ambient pressure, or greater, may be used, or pressures of from 100 kPa to 1000 kPa, or from 100 kPa to 500 kPa, or from 100 kPa to 300 kPa. At such conditions, the dehydrochlorination of PDC will produce HCl, monochloropropene isomers, and unreacted PDC.

The product stream from the vapor phase dehydrochlorination is cooled and partially condensed. The vapor stream is fed to a first separation column, e.g., a distillation column, operated at conditions effective to provide anhydrous HCl and monochloropropenes to an overhead line thereof. This stream is then fed to an anhydrous HCl purification column.

The top temperature of a separation column for the recovery of anhydrous HCl may typically be set below 0° C. or more preferably, can be set at a temperature of from −70° C. to −10° C. The bottom temperature of such a column is desirably set at from 10° C. to 150° C., or from 30° C. to 100° C., with the exact temperature dependent to some degree on the bottom mixture composition, as will be understood by those of ordinary skill in the art. The pressure of this purification column is desirably set above 200 kPa or preferably, from 350 kPa to 2000 kPa, or more preferably from 500 kPa to 1000 kPa. The bottom stream of a column operated at such conditions would be expected to contain excess chlorine, unreacted monochloropropene intermediates, while the overhead stream would be expected to comprise anhydrous HCl.

The bottom stream of the first separation column comprising unreacted PDC and heavier intermediates and byproducts may be fed to a further separation column, as desired, according to the particular embodiment being practiced. In this column, unreacted PDC is recovered in the overhead stream and recycled to the gas-phase dehydrochlorination reactor. The bottom stream, comprising heavier byproducts, is provided to a liquid phase chlorination reactor.

One example of a suitable liquid phase chlorination reactor would be a batch or continuous stirred tank reactor with an internal cooling coil. A shell and multitube exchanger followed by vapor liquid disengagement tank or vessel can also be used. The suitable reaction conditions for liquid phase chlorinations include, e.g., temperatures of from ambient temperature (e.g., 20° C.) to 200° C., or from 30° C. to 150° C., or from 40° C. to 120° C. or from 50° C. to 100° C. Ambient pressure, or pressures of from 100 kPa to 1000 kPa, or from 100 kPa to 500 kPa, or from 100 kPa to 300 kPa may be used. In some embodiments, one or more catalysts comprising $FeCl_3$ or $AlCl_3$ or free radical initiator comprising AIBN may be used in the chlorination reactor, while in others, their use is without benefit.

The liquid phase chlorinations may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, monochloropropene intermediates may be recycled back to the chlorination reactor from one separation column and/or di- and trichloropropene intermediates may be recycled from another separation column. Or, the chlorination reactor may be provided with a feedstock of any appropriate solvent for chlorination reactions, such as, e.g., carbon tetrachloride, sulfuryl chloride, 1,1,2,3-pentachloropropane, 1,1,2,2,3,3-hexachloropropane, other hexachloropropane isomers, or a combination of these.

In some embodiments, the bottoms stream from the HCl recovery column comprising monochloropropene may be fed to a chlorination reactor together with a recycle stream comprising tri and tetrachloropropane intermediate. The chlorinated organic product of the chlorination reactor is then fed to a separation column would desirably be operated at conditions sufficient to produce an overhead stream comprising 1,1,2,3-tetrachloropropane (1123) and other chlorinated propanes with boiling points lower than 1123 to the chlorination reactor, while the bottoms stream therefrom, typically comprising 1,1,2,2,3-pentachloropropane (11223), 1,1,1,2,3-pentachloropropane (11123), and other pentachloropropanes, and heavier byproducts, may be fed to a separation column for the recovery of pentachloropropane intermediates in an overhead stream thereof, and removal of 1,1,2,3,3-pentachloropropane and heavier byproducts in a bottoms stream. The overhead stream comprising 11223 and 11123 can then be fed into a dehydrochlorination reactor where 11123 can be converted to TCPE and anhydrous HCl using, e.g., a catalyst such as $FeCl_3$. HCl can be recovered from the dehydrochlorination reactor overhead, and the bottom liquid product comprising TCPE and 11223 can then be fed with aqueous caustic into a subsequent dehydrochlorination reactor. In this reactor, at least a portion of any remaining 11223 can be converted to TCPE.

One exemplary process is shown in FIG. 1. As shown in FIG. 1, process 100 makes use of gas-phase dehydrochlorination reactor 110, liquid phase dehydrochlorination reactor 130 and 140, drying unit 142, liquid phase chlorination reactor 120, and separation columns 112, 114, 116, 122, and 124.

In operation, a feed stream comprising PDC is first fed to vapor phase dehydrochlorination reactor 110, operated at conditions suitable to produce HCl, monochloropropene isomers, and unreacted PDC. The product stream from the vapor phase dehydrochlorination is cooled and partially condensed. The vapor stream is then fed to separation column 112, which provides anhydrous HCl and monochloropropenes through an overhead line to separation column 114, for purification and recovery of anhydrous HCl. The bottom stream of separation column 114, comprising excess chlorine and monochloropropene intermediates is provided to liquid phase 120.

The bottom stream from separation column 112, comprising unreacted PDC and heavier intermediates and byproducts, is fed to separation column 116. Separation column 116 provides unreacted PDC as an overhead stream that is recycled to gas-phase dehydrochlorination reactor 110. The bottoms stream from separation column 116 is provided to liquid phase chlorination reactor 120, along with the bottoms stream from separation column 114, and the overhead stream from separation column 122.

Liquid phase chlorination reactor 120 produces a bottom product stream comprising tetra- and pentachloropropanes, and heavier byproducts, which is fed to separation column 122. The overhead from 120 comprising excess chlorine, HCl, unreacted monochloropropenes, and PDC are recycled to separation unit 112.

The overhead stream from separation column 122, comprising 1,1,2,3-tetrachloropropane (1123) and lighter chlorinated propanes (with boiling points lower than 1123) is recycled to liquid phase chlorination reactor 120. The bottoms stream from separation column 122, comprising 1,1,2,2,3-pentachloropropane, other pentachloropropanes, and heavier byproducts, is provided to separation column 124 for the recovery of pentachloropropane intermediates in an overhead stream thereof, and removal of 1,1,2,3,3-pentachloropropane and heavier byproducts in a bottoms stream.

The overhead stream from separation column 124, comprising 11223- and 11123-pentachloropropane, is provided to liquid phase dehydrochlorination reactor 130 with a catalyst such as $FeCl_3$, which produces an overhead stream comprising HCl, which may be recycled to separation column 114 for the recovery of anhydrous HCl. The bottoms stream from dehydrochlorination reactor 130, comprising unreacted 11223-pentachloropropane and TCPE, is provided to liquid phase dehydrochlorination reactor 140 together with aqueous caustic. Dehydrochlorination reactor 140 is operated at conditions effective to crack the unreacted 11223-pentachloropropane from dehydrochlorination reactor 130 to TCPE. The product stream from dehydrochlorination reactor 140 is provided to drying unit 142, which provides TCPE as an overhead stream, and a bottoms aqueous waste stream.

The chlorinated and/or fluorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated and/or fluorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated and/or fluorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated and/or fluorinated propene is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 1,3,3,3-tetrafluoropropene via a catalyzed, gas phase reaction.

In the following examples, individual chloropropane isomers are identified by reference to the positions of the chlorine atoms, i.e., 112 indicates 1,1,2-trichloropropane, 1123 indicates 1,1,2,3-tetrachloropropane, 11223 indicates 1,1,2,2,3-pentachloropropane, and so on. For chlorinated propenes, similar nomenclature is used, with an "e" added as a suffix, e.g., 112e indicates 1,1,2-trichloropropene, 1123e indicates 1,1,2,3-tetrachloropropene, 11223e indicates 1,1,2,2,3-pentachloropropene, and so on.

Example I

PDC (1,2-dichloropropane) is evaporated at 250° C. and preheated before feeding to a tube heated to a achieve block furnace temperature of 525° C. At 30 psig the reaction residence time is about 16 seconds. The furnace is a 40" straight length of 0.5" OD tube made of SS347 alloy with temperature measurement positions at 10", 20", and 30" positions within the furnace tube. The tube is centered in an aluminum heating block assembly machined to tightly fit the outer surface of the tube.

The product gas is sampled using an on-line GC analysis. The measured dehydrochlorination rate is 43.2% with monochloropropenes overall selectivity of 97.53%. The selectivity of the monochloropropene isomers is listed in table 1. Other minor byproducts produced include propylene, benzene, 1,5-hexadiene, 1,3-cyclohexadiene, and 3-chloro-1,5-hexadiene, at selectivities of 0.54%, 0.71%, 0.19%, and 0.11%, respectively.

This example shows that the gas phase dehydrochlorination of PDC produces predominantly 3-chloropropene and a mixture of 1-chloropropene isomers.

TABLE I

Selectivity of monochloropropene isomers of PDC cracking at 16 s residence time, 525° C., and 30 psig

| % selectivity | Product |
|---|---|
| 3.69 | 2-chloropropene |
| 23.86 | cis-1-chloropropene |
| 13.6 | trans-1-chloropropene |
| 56.37 | 3-chloropropene |

Example II

In this example, the same reactor in example I is used to study the impact of increasing pressure from 30, 60, and 100 psig at 535° C. and 11 second residence time. While the observed cracking rate, or conversion, of PDC was found to be independent of pressure, the 2-chloropropene selectivity increased linearly from 3.2% at 30 psig to 5.2% at 100 psig. At the same time, allyl chloride selectivity linearly decreased from 56.8% at 30 psig to 53% at 100 psig.

Example III

In this example, the same reactor in example I is used to study the impact of residence time and cracking rate on monochloropropene selectivity. The results are shown in Table II. As shown, selectivity greater than 97% to the desired monochloropropenes is obtained at residence times from 6 to 16 seconds and temperatures from 515° C. to 555° C. Cracking rates above 50% are found to result in an exponential decline of the PDC yield to monochloropropene and increase the tendency for heavy formation of tar and carbon deposits on the reactor internal wall.

TABLE II

The impact of residence times and reaction temperatures on the PDC conversions and product selectivities.

| Residence time (s) | 16 | 6 | 6 | 11 | 16 |
|---|---|---|---|---|---|
| Temperature (° C.) | 525 | 545 | 555 | 535 | 515 |
| Pressure (psig) | 30 | 30 | 30 | 30 | 30 |
| Conversion | 43.2 | 37.1 | 46.33 | 45.34 | 35.85 |
| $C_3H_5Cl$ sel(%) | 97.52 | 97.74 | 97.32 | 97.10 | 97.99 |

The invention claimed is:

1. A process for the production of chlorinated propenes from one or more chlorinated alkanes comprising 1,2-dichloropropane, comprising at least one gas phase dehydrochlorination step that is the first reaction step, wherein the gas phase dehydrochlorination is carried out without the use of a catalyst and at a pressure greater than ambient, wherein the gas phase dehydrochlorination produces one or more monochloropropenes; and wherein the one or more monochloropropenes are separated from the 1,2-dichloropropane, and after separation, the one or more monochloropropenes are subjected to at least one liquid phase chlorination step.

2. The process of claim 1, wherein the chlorinated propenes comprise dichloropropenes, trichloropropenes, and/or tetrachloropropenes.

3. The process of claim 1, wherein the one or more chlorinated alkanes further comprise 1,2,3-trichloropropane.

4. The process of claim 1, comprising at least one additional dehydrochlorination step.

5. The process of claim 4, wherein at least one additional dehydrochlorination step is conducted in the liquid phase, in the presence of one or more catalysts.

6. The process of claim 4, wherein at least one additional dehydrochlorination step is conducted in the liquid phase, in the presence of caustic.

7. The process of claim 1, wherein at least one chlorination step is conducted in the gas phase.

8. The process of claim 1, wherein at least one chlorination step is conducted in the liquid phase.

9. The process of claim 1, wherein HCl is generated as a byproduct.

10. The process of claim 9, wherein HCl is recovered as anhydrous HCl.

11. The process of claim 1, wherein the dehydrochlorination step is conducted at 200° C. or greater.

12. The process of claim 1, wherein the 1,2-dichloropropane conversion is from 30% to 70%.

13. The process of claim 12, wherein the 1,2-dichloropropane conversion is from 40% to 60%.

* * * * *